United States Patent [19]

Rasche et al.

[11] Patent Number: 4,939,245

[45] Date of Patent: Jul. 3, 1990

[54] PROCESS FOR THE DIRECT PRODUCTION OF GLYSOSIDE PRODUCT IN THE PRESENCE OF SOLID SACCHARIDE

[75] Inventors: John F. Rasche; Carl E. Pickens; Patrick M. McCurry, Jr., all of Decatur, Ill.

[73] Assignee: Henkel Kommanditgesellschaft auf Aktien, Duesseldorf-Holthausen, Fed. Rep. of Germany

[21] Appl. No.: 287,953

[22] Filed: Dec. 21, 1988

[51] Int. Cl.$^5$ .................. C07G 3/00; C07H 1/00
[52] U.S. Cl. .................. 536/18.6; 536/124; 536/18.5
[58] Field of Search ............ 536/18.6, 124, 18.5

[56] References Cited

U.S. PATENT DOCUMENTS

| | | | |
|---|---|---|---|
| 3,219,656 | 11/1965 | Boettner | 260/210 |
| 3,547,828 | 12/1970 | Mansfield et al. | 252/351 |
| 3,598,865 | 8/1971 | Lew | 260/210 |
| 3,707,535 | 12/1972 | Lew | 260/210 |
| 3,772,269 | 11/1973 | Lew | 260/210 |
| 3,839,318 | 10/1974 | Mansfield | 260/210 |
| 3,974,138 | 8/1976 | Lew | 536/4 |
| 4,349,669 | 9/1982 | Klahr et al. | 536/127 |
| 4,393,203 | 7/1983 | Mao et al. | 536/124 |
| 4,472,170 | 9/1984 | Hellyer | 44/51 |
| 4,510,306 | 4/1985 | Langdon | 536/127 |
| 4,597,770 | 7/1986 | Forand et al. | 44/51 |
| 4,704,453 | 11/1987 | Lorenz et al. | 536/18.6 |
| 4,713,447 | 12/1987 | Letton | 536/18.6 |

FOREIGN PATENT DOCUMENTS

| | | |
|---|---|---|
| 92355 | 4/1983 | European Pat. Off. . |
| 96917 | 5/1983 | European Pat. Off. . |
| 132043 | 6/1984 | European Pat. Off. . |

*Primary Examiner*—Ronald W. Griffin
*Assistant Examiner*—Everett White
*Attorney, Agent, or Firm*—Ernest G. Szoke; Wayne C. Jaeschke; Daniel S. Ortiz

[57] ABSTRACT

The invention is a process for preparing a glycoside product by reacting an alcohol having 4 to 30 carbon atoms with a saccharide or oligosaccharide in the presence of an acid catalyst wherein an undissolved phase comprising the saccharide or oligosaccharide is present in the reaction mixture during the process.

7 Claims, No Drawings

PROCESS FOR THE DIRECT PRODUCTION OF GLYSOSIDE PRODUCT IN THE PRESENCE OF SOLID SACCHARIDE

BACKGROUND OF THE INVENTION

1. Field of the Invention:

The present invention pertains to the preparation of glycoside products by the acid catalyzed reaction of an alcohol reactant and a saccharide reactant. More particularly, the invention is a process for the preparation of glycoside products in a two phase system comprising a liquid phase and a solid phase containing saccharide reactant.

2. Statement of Related Art:

Glycoside products such as alkyl or alkenyl polyglycosides have been known for many years. The materials have not achieved outstanding commercial success because the products generally had a dark color and a low degree of polymerization. In the manufacture of glycoside products from water-soluble monosaccharide and polysaccharide starting materials such as glucose, maltose, sucrose, xylose, lactose and the like by the acid catalyzed reaction with an alcohol reactant such as ethylhexyl alcohol, octyl alcohol, decyl alcohol, dodecyl alcohol, hexadecyl alcohol and the like, it has generally been the practice to introduce the saccharide reactant into the reaction mixture in an amount which would dissolve in the liquid phase and would be completely reacted during the process so that no solid or undissolved phase containing the saccharide reactant remained in the reaction mixture. It was believed necessary not to have a large excess of solid or undissolved phase, containing the saccharide reactant, present during the process and especially where the reaction had proceeded to the point where recovery of the glycoside product was required.

Many processes are known in the art for preparing the glycoside products of the present invention by the reaction of an alcohol and a saccharide reactant. The processes generally utilize solubilizing agents to maintain all of the saccharide reactant in solution during the process or carry out the reaction to the point that no undissolved saccharide reactant remains at the end of the reaction portion of the process.

U.S. Pat. No. 3,598,865 to Lew (Aug. 10, 1971) utilizes a latent solvent to dissolve the saccharide reactant and provide a homogeneous mixture with the alcohol reactant.

U.S. Pat. No. 3,707,535 to Lew (Dec. 26, 1972) discloses the use of a solvent to aid in solubilizing the saccharide reactant.

U.S. Pat. No. 3,974,138 to Lew (Aug. 10, 1976) controls the ratio of alcohol to saccharide so that the product solution produced by the process is clear and contains no undissolved saccharide reactant.

European patent publication 96,917 to Farris Dec. 28, 1983) discloses the incremental addition of the saccharide reactant to the reaction mixture so that no solid phase is present.

European patent publication 106,743.5 (Jan. 13, 1988) discloses adding a sufficient amount of butyl oligoglycoside to the reaction mixture so that a homogeneous reaction mixture is formed.

Glycoside products can be prepared by reacting a long chain alcohol with a saccharide reactant (e.g., a monosaccharide or a material hydrolyzable to a monosaccharide) at an elevated temperature in the presence of an acid catalyst by processes such as disclosed for example, U.S. Pat. No. 3,219,656 to Boettner (issued Nov. 23, 1965); U.S. Pat. No. 3,547,828 to Mansfield et al. (issued Dec. 15, 1970); U.S. Pat. No. 3,772,269 to Lew (issued Nov. 13, 1973); U.S. Pat. No. 3,839,318 to Mansfield (issued Oct. 1, 1974); U.S. Pat. No. 4,349,669 to Klahr (issued Sept. 14, 1982); U.S. Pat. No. 4,393,203 to Mao et al. (issued July 12, 1983); U.S. Pat. No. 4,472,170 to Hellyer (issued Sept. 18, 1984); U.S. Pat. No. 4,510,306 to Langdon (issued April 9, 1985); U.S. Pat. No. 4,597,770 to Forand et al. (issued July 1, 1986; U.S. Pat. No. 4,704,453 to Lorenz et al. (issued Nov. 3, 1987); U.S. Pat. No. 4,713,447 to Letton (issued Dec. 15, 1987); published European Application No. 83302002.7 (EPO Publication No. 0092355; Vander Burgh et al; published Oct. 26, 1983); published European Application No. 83200771.0 (EPO Publication No. 0096917; Farris; published Dec. 28, 1983); and published European Application No. 84303874.6 (EPO Publication 0132043; Davis et al; published Jan. 23, 1985).

BRIEF SUMMARY OF THE INVENTION

Applicants have unexpectedly discovered that glycoside products can be prepared by the present invention, which have a low color at a fast reaction rate by including in the reaction mixture, at all times during the reaction, a solid or undissolved saccharide reactant.

According to the present invention a process for preparing a glycoside product of the formula $ROG_x$ wherein R is a residue of an alcohol having from 4 to 30 carbon atoms, 0 is oxygen, G is the residue of a reducing saccharide or oligosaccharide and x is the average degree of polymerization (DP) of from about 1–3 by reacting an alcohol having from 4 to 30 carbon atoms with a saccharide or oligosaccharide is provided. The process comprises:

(1) forming a mixture comprising an acid catalyst, a liquid phase containing an alcohol having from 4 to 30 carbon atoms and a saccharide or a oligosaccharide, and an undissolved phase containing the saccharide or oligosaccharide;

(2) reacting the mixture to form the glycoside product under conditions in which the undissolved phase containing the saccharide or oligosaccharide is present;

(3) separating the liquid phase from the undissolved phase; and (4) recovering the glycoside product from the liquid phase.

In a preferred embodiment of the invention, the liquid phase, separated from a solid undissolved phase, is further reacted to reduce the amount of dissolved unreacted saccharide in the liquid phase.

The glycoside product can be separated from the unreacted alcohol and other volatile products in the liquid phase by heating the mixture under reduced pressure. Preferably, the liquid phase is heated at an elevated temperature and a reduced pressure in a wiped film evaporator. In another embodiment of the invention, a solvent is added to the mixture to aid in removal of water and separation of unreacted alcohol from the glycoside product of the invention.

DESCRIPTION OF THE INVENTION

The glycoside product of the present invention comprises compositions of the formula:

ROG$_x$ wherein R is a residue of an alcohol having from 4 to 30 carbon atoms, O is oxygen, G is a glycoside residue and x is the average degree of polymerization (DP) and is a number of from about one to three.

The alcohols suitable for use in the process of the present invention contain from 4 to 30 carbon atoms and preferably about 8 to about 20 carbon atoms, and include monohydric alcohols and dihydric alcohols. The alcohols useful in the practice of the present invention can be saturated aliphatic, unsaturated aliphatic or aromatic in character.

The preferred alcohols are alcohols such as butyl alcohol, octy alcohol, 2-ethylhexyl alcohol, nonyl alcohol, decyl alcohol, undecyl alcohol, dodecyl alcohol, eicosyl alcohol, pentacosyl alcohol, oleyl alcohol, linoleyl alcohol, isoborneal alcohol, hydroabietyl alcohol tetradecyl alcohol, hexadecyl alcohol, octadecyl alcohol, their isomers and the like. The alcohols can be linear or branched and can be secondary alcohols as long as the alcohol is not sterically hindered from reacting with the saccharide. Alkoxylated alcohols including ethoxylated and propoxylated alcohols can be use in the process.

Unsaturated alcohols and alcohols containing an aromatic moiety such as alkyl and alkenyl substituted benzyl alcohols, wherein the alkyl or alkenyl groups contain from about 1 to about 20 carbon atoms, alkoxylated phenols having from about 1 to 20 alkoxy groups such as ethoxy, propoxy, butoxy groups and the like are useful in the practice of the present invention. Alcohols such as phenoxyethanol, phenoxypolyethoxyethanol containing five ethoxy groups and the like are useful.

The saccharide materials useful in the practice of the present invention include monosaccharides such as glucose, lactose, mannose, xylose, fructose and the like.

Oligosaccharide materials such as sucrose, maltose, maltotriose, cellobiose, melibiose, and the like are useful in the practice of the present invention. Mixtures of the mono and oligosaccharide materials are also useful in the practice of the present invention. Preferred saccharides for use in the practice of the present invention include glucose and sucrose.

In the first step of the process of the present invention, a mixture comprising an acid catalyst, a liquid phase containing an alcohol having 4 to 30 carbon atoms and a saccharide or oligosaccharide is formed. The process of the present invention is generally carried out in a reaction mixture having a low water content.

The liquid phase can contain a liquid composition which is immiscible with water and which preferably has a boiling point lower than the boiling point of the alcohol. Organic liquids such as benzene, toluene, xylene, and the like have been found useful. The water immiscible liquids aid in controlling the viscosity of the reaction mixture and aid in removing the water formed in the process.

If the saccharide utilized in the process is in the form of a solution in water or a solid containing water of hydration, the saccharide can be first mixed with the alcohol. The mixture of the alcohol and the aqueous or water containing saccharide is then heated to an elevated temperature under a reduced pressure to remove the water from the mixture and provide a mixture of the alcohol and the solid or undissolved saccharide reactant having a low water content. The reaction mixture should contain less than about 1.0% by weight water, preferably less than about 0.5 by weight water, more preferably less than about 0.25% by weight water and most preferably less than about 0.1% by weight water. Preferably the undissolved saccharide is in a solid form rather than as a melt or syrup.

The acid catalyst is preferably not added to the mixture of the alcohol and saccharide until the water content of the mixture has been reduced to the predetermined level. If the alcohol does not contain water and the saccharide is a crystalline material with a low water content, the alcohol and the saccharide reactant can be mixed and the catalyst added to the mixture.

An excess of the saccharide is mixed with the alcohol; that is, an amount of the saccharide in excess of the amount soluble in the liquid phase. Generally, from about 1.25 to about 3 times the amount of saccharide to be reacted with the alcohol is present in the reaction mixture. However, the process of the present invention only requires that a sufficient amount of saccharide reactant be present in the mixture during the reaction so that an undissolved saccharide containing phase is present and when the reaction has proceeded to the desired point, the reaction mixture contains the saccharide reactant present in the undissolved form.

It is critical that undissolved saccharide be present in the reaction mixture during the process. All of the saccharide can be added initially or the saccharide can be added incrementally during the reaction portion of the process. It is preferred that all or at least about 50% of the saccharides be present in the reaction mixture at the beginning of the process. In a continuous process, it is preferred that all of the saccharide be present at the beginning of the reaction portion of the process.

The presence of undissolved saccharide in the reaction mixture, while the polyglycoside product is being formed, insures that the liquid phase contains dissolved saccharide at a concentration near its solubility limit. The processes which are homogenous, have a reduced concentration of saccharide as the process progresses. The high concentration of dissolved saccharide is believed to provide for more rapid reaction between the alcohol and the saccharide.

As is well understood in the art, the reaction between the alcohol and the saccharide reactant is carried out at an elevated temperature under a reduced pressure so that the water formed, by reaction between the alcohol and the saccharide or between the saccharide moieties, is removed from the reaction mixture substantially as soon as it is formed. It is important in the process of the present invention that the amount of water in the reaction mixture be maintained at a relatively low level. If the amount of water in the reaction mixture becomes high, the saccharide reactant can form a syrup phase which is undesirable and promotes the formation of color bodies and polysaccharide materials.

The acid catalysts useful in the process of the present invention include the mineral acids such as hydrochloric acid, sulfuric acid and the like and the organic acids such as alkyl benzene sulfonic acid, linear alkyl sulfonic acids, alkyl phenyl sulfonic acids and alkyl naphthyl sulfonic acids. The catalyst is generally present in the reaction mixture in an amount of from about 0.01 to about 5% by weight of the alcohol in the reaction mixture.

The reaction mixture is generally heated to a temperature in the range of from about 85° to about 200° C. and preferably from about 100° to about 150° C. and more preferably 100°–120° C. and maintained at a pressure in the range of from about 3 millimeters of mercury absolute pressure to atmospheric pressure. The temperature and the pressure maintained on the reaction mixture, to ensure removal of the water formed during the reaction, is dependent upon the boiling point of the alcohol and any solvents present and their concentration in the reaction mixture. Lower molecular weight alcohols generally require lower temperatures and higher pressures.

After the reaction has proceeded to the point where the concentration of the glycoside product in the liquid phase has reached the desired concentration and the degree of polymerization (DP), the value of x, has achieved the desired range, the liquid phase is separated from the undissolved saccharide portion of the reaction mixture. The concentration of glycoside product in the liquid phase is generally from about 10 to about 60% by weight and preferably from about 20 to 50 percent by weight and most preferably from about 25 to about 45 percent by weight of the liquid phase. A higher concentration of glycoside in the liquid phase provides glycoside products having a higher average DP.

The undissolved and preferably solid saccharide reactant can be separated from the liquid phase by known methods of liquid solid separations such as filtration, settling, centrifuging, cyclone separation, microfiltration, combinations thereof and the like.

The liquid phase contains the unreacted alcohol, the glycoside product, the catalyst and other materials which may be soluble in the alcohol or the reaction mixture. Generally, the liquid phase will contain unreacted saccharide reactant which is soluble in the liquid phase. The liquid phase which has been separated from the undissolved saccharide can be maintained at an elevated temperature and a reduced pressure to react the saccharide in solution to glycoside product and provide glycoside product having a lower dissolved saccharide content. The reaction can be carried out at a temperature of from about 90° to about 150° C. at a pressure in the range of 3mm mercury absolute to about atmospheric pressure. After the additional reaction and neutralization, the unreacted alcohol is separated from the glycoside product by heating the mixture at an elevated temperature and a reduced pressure. Preferably, the mixture is heated in a wiped film evaporator at a pressure in the range from about 0.1mm to about 30 millimeters preferably from about 1-5mm of mercury absolute. The glycoside product can be finished in the normal manner such as by decolorization, color stabilization and the like.

The process of the invention can be operated in a continuous manner by introducing a mixture of alcohol, saccharide and acid catalyst continuously into a reaction zone, continuously withdrawing a portion of the reaction mixture from the reaction zone, separating the undissolved saccharide from the liquid phase and recovering the glycoside product either directly or after further conversion of the residual soluble reducing sugars to glycoside product If the alcohol and saccharide contain water, a dry mixture should be provided to the reaction zone by the drying step of heating the alcohol and saccharide under a reduced pressure to remove the water from the mixture before mixing with the acid catalyst.

The continuous process is advantageous since the saccharide is generally more soluble in a mixture of alcohol and glycoside product, than in alcohol alone so that the concentration of saccharide in the liquid phase is higher than it is initially in a batch process where no glycoside product is present at the beginning of the process.

The products of the process of the present invention are useful as surfactants or precursors for forming polyglycoside products having a higher molecular weight hydrocarbon group attached thereto by means of a transacetalization process.

The process of the present invention is illustrated by the examples which follow. The examples are by way of illustration and are not intended to limit the process of the present invention.

EXAMPLE 1

A mixture of 606.3 grams of Neodol ® 23 (3.125 mols of a C12-13 alcohol) and 247.5 grams of Staleydex ® 333 (1.25 mols of a dextrose hydrate) was formed at room temperature. The pressure on the mixture was reduced to 32 millimeters of mercury absolute and the temperature was raised to 110° C. over three hours. Dehydration occurred and 22.5 milliliters of water were collected by distillation. 1.19 grams (0.00625 mols) of paratoluene sulfonic acid monohydrate were added to the mixture. Samples were removed periodically, neutralized with sodium acetate and filtered. Two and a half hours after catalyst addition, the filtrate removed from the reaction mixture had a total solids content of 26.88%. The filtrate contained 3.9% total polar solids, the bulk of which was dextrose. The filtrate had an extinction coefficient of less than 0.1 and was clear.

The example clearly shows that the process of the present invention can produce a polyglyoside product having a low color and at a rapid rate of reaction.

The extinction coefficient is the calculated absorbance of a theoretical solution containing one gram of solid material per cubic centimeter of solution measured at a 470 nm wavelength. The formula for determining the extinction coefficient is as follows:

$$E_{470} = \frac{A}{(c \times l)} \text{ wherein:}$$

A = measured absorbence @ 470nm
c = concentration in grams per cm$^3$
l = path length in centimeters and
$E_{470}$ = the extinction coefficient.

The lighter colored materials have the lower extinction coefficients.

EXAMPLE 2

A mixture of 585.8 grams of Lorol 1214A (3.04 moles of a $C_{12}$, $C_{14}$, $C_{16}$ alcohol) and 299.0 grams of Staleydex ® 333 (1.52 moles of a dextrose hydrate) was formed at room temperature. The pressure on the mixture was reduced to 20 millimeters of mercury absolute and the temperature was raised to 107° C. over two and one-quarter hours. Dehydration occurred and 17.5 milliliters of water were collected by distillation. An amount of 6.45 grams (0.0070 moles) of 51% dinonylnaphthalene sulfonic acid in heptane were added to the mixture. Samples were removed periodically, neutralized with sodium acetate, and filtered. Three (3) hours after catalyst addition, the filtrate removed from the reaction mixture had a total dissolved solids content of 40.14%, a color of less than 0.2 (extinction coefficient) and was clear.

As can be seen from the examples the process of the present invention provides a process which produces a glycoside product having a low color. The process of the invention also provides for rapid reaction between the saccharide and alcohol to produce the glycoside product in reduced reaction times.

We claim:

1. A process for preparing a glycoside product by reacting an alcohol having from 4 to 30 carbon atoms with a saccharide or oligosaccharide reactant, said process comprising:
   (1) forming a mixture comprising an acid catalyst, a liquid phase containing an alcohol having from 4 to 30 carbon atoms and a solid phase containing an amount of the saccharide or oligosaccharide reactant in excess of the amount of saccharide or oligosaccharide which is soluble in the liquid phase;
   (2) reacting the mixture to form the glycoside product under conditions in which the solid phase containing the saccharide or oligosaccharide reactant is present;
   (3) separating the liquid phase from the solid phase and
   (4) recovering the glycoside product from the liquid phase.

2. A process of claim 1 wherein the liquid phase, separated from the undissolved phase, is further reacted to reduce the amount of dissolved saccharide in the liquid phase which has not reacted with the alcohol.

3. A process of claim 2 wherein the alcohol comprises at least one alcohol having from 8 to 30 carbon atoms.

4. A process of claim 3, wherein the alcohol is an aliphatic alcohol.

5. A process of claim 1 wherein the alcohol comprises at least one alcohol having from 8 to 30 carbon atoms.

6. A process of claim 5 wherein the alcohol is an aliphatic alcohol.

7. A process of claim 1 which comprises:
   (1) forming a mixture of the alcohol and the saccharide or oligosaccharide;
   (2) heating the mixture under a reduced pressure to reduce the amount of water in the mixture;
   (3) adding an acid catalyst to the mixture;
   (4) reacting the mixture at an elevated temperature under conditions in which undissolved saccharide reactant is present, and reduced pressure to remove water from the reaction mixture substantially as it is formed;
   (5) separating the liquid phase from the undissolved saccharide phase;
   (6) further reacting the liquid phase, separated from the undissolved saccharide phase, to reduce the amount of dissolved saccharide in the liquid phase; and
   (7) recovering the glycoside product from the liquid phase.

* * * * *